(12) United States Patent
Hallen

(10) Patent No.: US 12,336,690 B2
(45) Date of Patent: Jun. 24, 2025

(54) IMAGING TOOL TO SUPPORT EYE SURGERY

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 919 days.

(21) Appl. No.: 17/451,346

(22) Filed: Oct. 19, 2021

(65) Prior Publication Data
US 2022/0125284 A1 Apr. 28, 2022

Related U.S. Application Data

(60) Provisional application No. 63/106,435, filed on Oct. 28, 2020.

(51) Int. Cl.
*A61B 1/05* (2006.01)
*A61B 1/06* (2006.01)
*A61F 9/007* (2006.01)

(52) U.S. Cl.
CPC .......... *A61B 1/05* (2013.01); *A61B 1/06* (2013.01); *A61F 9/007* (2013.01)

(58) Field of Classification Search
None
See application file for complete search history.

(56) References Cited

U.S. PATENT DOCUMENTS

| | | | |
|---|---|---|---|
| D380,550 S * | 7/1997 | Dennewill | D24/185 |
| 5,754,313 A * | 5/1998 | Pelchy | A61B 1/051 |
| | | | 358/473 |
| 5,857,963 A * | 1/1999 | Pelchy | A61B 1/051 |
| | | | 600/109 |
| 7,192,429 B2 * | 3/2007 | Trembly | A61B 18/14 |
| | | | 606/41 |
| 8,157,797 B2 | 4/2012 | Boukhny | |
| 8,372,726 B2 * | 2/2013 | de Graff | H01L 21/30 |
| | | | 438/457 |
| 8,814,854 B2 | 8/2014 | Jia | |
| 9,125,720 B2 | 9/2015 | Jia | |
| 9,295,384 B2 | 3/2016 | Wheatley et al. | |
| 9,839,749 B2 | 12/2017 | Johnson | |
| 10,667,685 B2 * | 6/2020 | Chang | A61B 3/117 |
| 2001/0055462 A1 * | 12/2001 | Seibel | A61B 1/00048 |
| | | | 385/33 |

(Continued)

OTHER PUBLICATIONS

Alcon Surgical Retina Product Catalog, 2019 (36 pages).

*Primary Examiner* — John P Leubecker
*Assistant Examiner* — Jae Woo
(74) *Attorney, Agent, or Firm* — PATTERSON + SHERIDAN, LLP

(57) ABSTRACT

An imaging tool with a tubular implement of minimal diameter for locating in a patient's eye and to extend an image capturing platform therefrom. The platform is uniquely sized for storage within the lumen or inner diameter of the implement, such as a thin film image sensor. However, a microchip package having a bulk footprint too large for the inner diameter of the implement may be displaced to another location of the tool such as within the adjacent, more sizeable handpiece or housing. Further, the platform may be expanded upon being exposed to the interior of the eye by the extending thereinto. Thus, an increased surface and pixel count may be provided for the imaging.

10 Claims, 5 Drawing Sheets

(56) References Cited

U.S. PATENT DOCUMENTS

| | | | |
|---|---|---|---|
| 2003/0142934 A1* | 7/2003 | Pan | G01B 9/0205 |
| | | | 385/116 |
| 2005/0043587 A1* | 2/2005 | Fujimori | A61B 1/00032 |
| | | | 600/156 |
| 2007/0208422 A1* | 9/2007 | Walter | A61F 2/148 |
| | | | 623/5.11 |
| 2007/0264732 A1* | 11/2007 | Chen | B81C 3/008 |
| | | | 29/25.35 |
| 2010/0312069 A1* | 12/2010 | Sutherland | A61B 17/0218 |
| | | | 600/245 |
| 2014/0107459 A1 | 4/2014 | Lind et al. | |
| 2015/0057548 A1* | 2/2015 | Kaufman | G01J 5/041 |
| | | | 600/473 |
| 2016/0077008 A1* | 3/2016 | Takasu | A61B 1/00186 |
| | | | 348/77 |
| 2016/0338574 A1* | 11/2016 | Fujimori | G02B 23/02 |
| 2017/0041576 A1* | 2/2017 | Kobayashi | A61B 1/00009 |
| 2017/0172694 A1 | 6/2017 | Dos Santos | |
| 2019/0029497 A1 | 1/2019 | Mirza et al. | |
| 2021/0057649 A1* | 2/2021 | Enoki | C07D 401/14 |
| 2021/0093177 A1 | 4/2021 | Anderson et al. | |
| 2024/0016515 A1* | 1/2024 | Nakamura | H04N 23/555 |
| 2024/0280800 A1* | 8/2024 | Tully | H04N 23/55 |

\* cited by examiner

IMAGING TOOL TO SUPPORT EYE SURGERY

PRIORITY CLAIM

This application claims the benefit of priority of U.S. Provisional Patent Application Ser. No. 63/106,435 titled "IMAGING TOOL TO SUPPORT EYE SURGERY," filed on Oct. 28, 2020, whose inventor is Paul R. Hallen, which is hereby incorporated by reference in its entirety as though fully and completely set forth herein.

BACKGROUND

Over the years, many dramatic advancements in the field of eye surgery have taken place. However, regardless of the particular procedure, a few different types of tools are generally employed. For example, an interventional tool that is tasked with directly engaging with and affecting a part of the eye will be utilized. A common example of such a tool is a vitrectomy probe utilized in a vitrectomy. A vitrectomy is the removal of some or all of the vitreous humor from a patient's eye. In some cases, where the surgery was limited to removal of clouded vitreous humor, the vitrectomy may constitute the majority of the procedure. However, a vitrectomy may accompany cataract surgery, surgery to repair a retina, to address a macular pucker or a host of other issues.

The vitreous humor itself is a clear gel that may be removed by an elongated probe when inserted through a pre-placed cannula at the eye. More specifically, the probe includes a central channel for removal of the vitreous humor. Further, the cannula provides a structurally supportive conduit strategically located at an offset location at the front of the eye, such as the pars plana. In this way, the probe may be guidingly inserted into the eye in a manner that avoids damage to the patient's lens or cornea.

Of course, in order to achieve a successful vitrectomy or other such intervention, some additional tools may be required. For example, visualization of the vitrectomy may be aided by the insertion of a light instrument. Similar to the vitrectomy probe, this may be guided by another pre-placed cannula that is again positioned at an offset location. Depending on the nature of the intervention and the location of the eye targeted, external imaging of the procedure may be sufficient without further aid. For example, where the probe is directed toward the back of the eye to address a hemorrhage threat, a camera focused through the front of the eye may provide sufficient imaging of the back of the eye for the procedure.

Unfortunately, from an imaging standpoint, surgical procedures are not always directed at the back of the eye. Further, the standard setup is to have an interventional tool and a light instrument each reaching into the eye from safer incision offset locations near the front of the eye. This means that the ability to visualize and directly interact with regions near the front of the eye can be a challenge. The field of view provided to the surgeon is simply limited.

In order to address the limited field of view issue, a surgical mirror may be utilized to expand the field visible to the surgeon. Just as a dental mirror may be positioned within a patient's mouth to provide a view of an otherwise shielded location behind a row of teeth, so too may an eye surgical mirror be utilized. So, for example, a surgical mirror may be inserted through the eye at third offset location. The face of the mirror may be directed at an adjacent offset location and/or toward the front of the eye. In this way, the surgeon and external imaging device that are facing the front of the eye may nevertheless be provided with visualization of offset or even back surface locations at the front of the eye.

While a surgical mirror may be an effective aid to visualization for the surgeon, the quality remains limited. Recall that the mirror is revealing an indirect reverse image of an eye location to a camera that is itself external to the patient's eye being operated on. Certainly, it might seem much more ideal to simply position an endoscope imaging device directly into the patient's eye and orient the device toward the offset or front eye locations. Indeed, this might even seem preferable for visualizing any region of the eye, even locations at the back of the eye.

Unfortunately, the ability to utilize an endoscope for such procedures is highly undesirable. Recall that the pre-placed cannulas have been located at offset locations. They also involve secure placement at incisions that are of extremely limited size. In fact, the light instrument, vitrectomy probe, surgical mirror and any other device reaching into the eye are unlikely to be any larger than about 0.70 mm (millimeters) in diameter in order to fit through the cannula. This may be too small to accommodate an angled endoscope because of the associated instrumentation.

SUMMARY

An imaging tool to support eye surgery is provided. The tool includes a housing for physical manipulation by an eye surgeon. A tubular implement of no greater than about 0.7 mm in outer diameter extends from a distal end of the housing to reach into an eye of a patient during the surgery. The housing accommodates a microchip that is of a bulk footprint greater than an inner diameter of the implement. However, a thin-film image capturing platform is accommodated within the tubular implement with capacity to extend from therein for image capture of the eye. The platform is further configured for expanding upon this extending from within the implement.

DETAILED DESCRIPTION

In the following description, numerous details are set forth to provide an understanding of the present disclosure.

However, it will be understood by those skilled in the art that the embodiments described may be practiced without these particular details. Further, numerous variations or modifications may be employed which remain contemplated by the embodiments as specifically described.

Embodiments are described with reference to certain types of vitrectomy probe surgical procedures. In particular, a procedure in which vitreous humor is removed to address vitreous hemorrhage is illustrated. However, tools and techniques detailed herein may be employed in a variety of other manners. For example, embodiments of a vitrectomy probe as detailed herein may be utilized to address retinal detachments, macular pucker, macular holes, vitreous floaters, diabetic retinopathy or a variety of other eye conditions. Regardless, so long as the surgical procedure is aided by the use of an imaging tool with a thin-film image capturing platform that is extendable and/or expandable into the environment of the eye for direct imaging, appreciable benefit may be realized.

Figure 1:
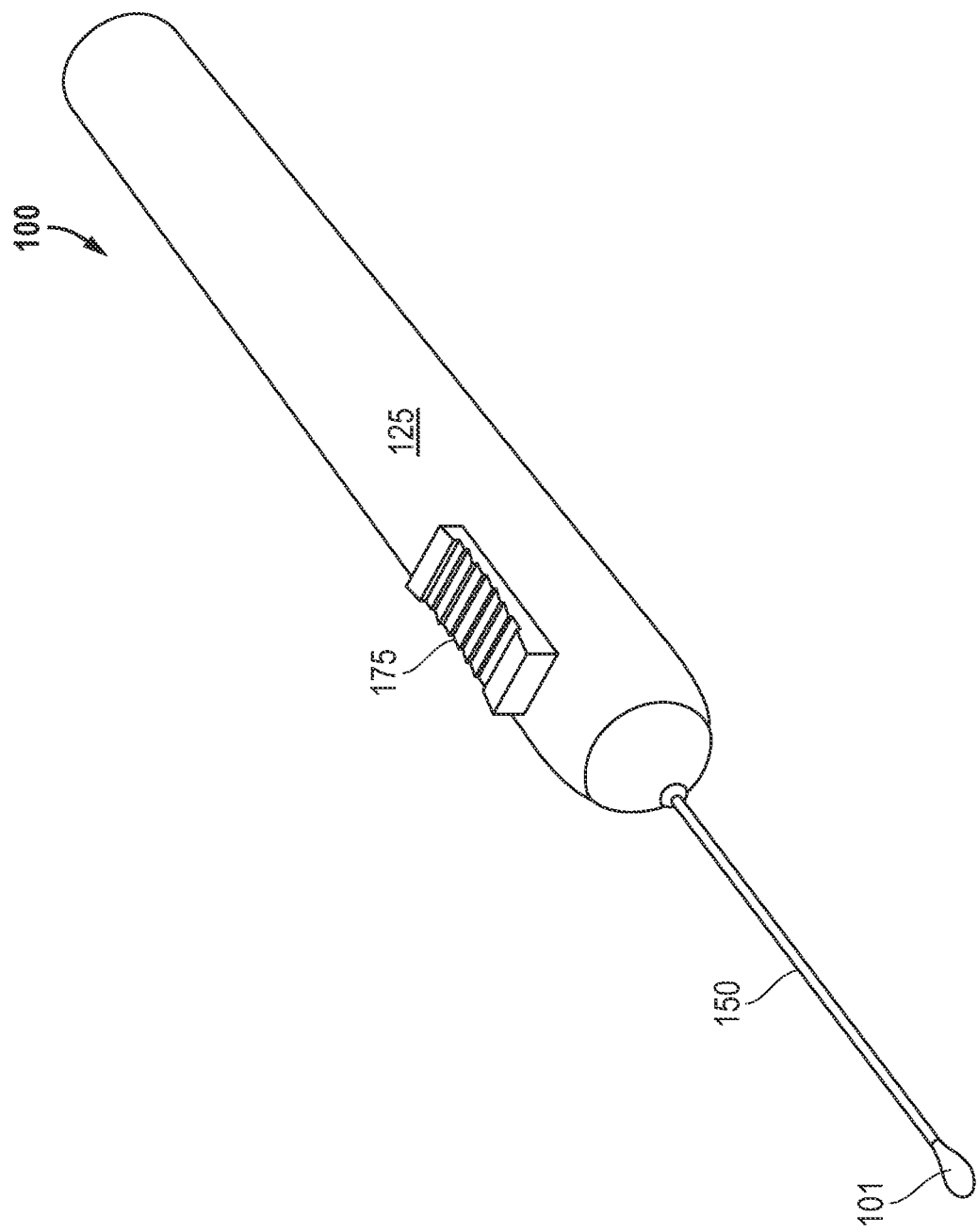
FIG. 1 is a perspective view of an embodiment of an imaging tool for eye surgery with a thin-film image capturing platform.
Figure 3:
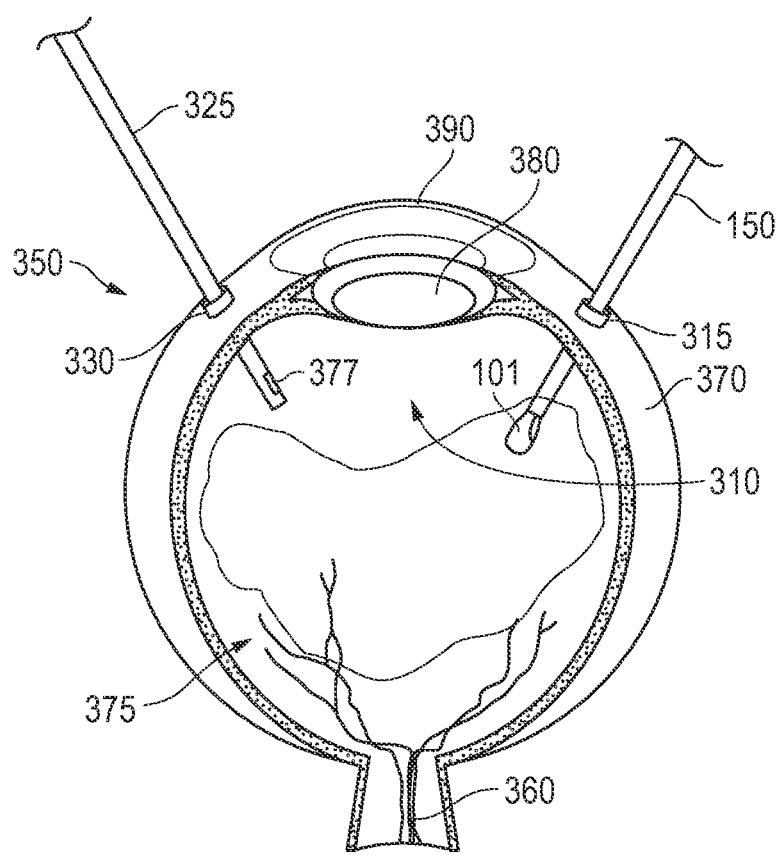
FIG. 3 is a side cross-sectional overview of a patient's eye during a vitrectomy procedure in which the imaging tool of FIG. 1 is utilized.

Referring now to FIG. 1, a perspective view of an embodiment of an imaging tool 100 is illustrated. In a broad sense, the tool 100 may be tailored for eye surgery as illustrated in FIG. 3. However, it is more specifically of note that the tool 100 includes a thin-film image capturing platform 101. As illustrated, the platform 101 has been extended from within a tubular needle implement 150. This implement 150 may be of no more than about 0.7 mm in outer diameter. Thus, as a practical matter, prior to extension (or upon retraction), the platform 101 is configured to collapse into a lumen of the implement 150 that is less than 0.7 mm in inner diameter, likely below about 0.9 mm. In this way, the larger profile of the extended and expanded platform 101 does not interfere with the minimally invasive nature of positioning the implement 150 through a preplaced cannula 315 during a surgical procedure as illustrated in FIG. 3.

The platform 101 may be supported by a flexibly expandable substrate of nitinol, a biocompatible elastomer or other suitable underlying support. However, it is the thin-film image sensor feature of the platform 101 that uniquely benefits the overall tool 100 for use in a minimally invasive surgery. With added reference to FIG. 2, not only might a thin-film image sensor be collapsible as alluded to above and detailed further below, but for the embodiment shown, a microchip imaging assembly 240 may be displaced from the location of the platform 101. That is, such an assembly 240 with a bulk footprint too large for positioning within the implement 150 may be displaced to another location such as within the housing 125 that is manually held by the surgeon during a procedure as illustrated in FIG. 3.

With further added reference to FIG. 2, unlike a conventional endoscope, thin-film image sensors such as those employed for the platform 101 of FIG. 1, may electrically couple to a microchip imaging assembly 240 through conventional cabled wiring or even by way of thin film circuitry with conductive traces. Regardless, the use of a thin-film platform 101 renders it practical to displace the larger bulk footprint assembly 240 to a nearby practical location. Thus, an actuator 175 may be used to extend and expand the collapsible platform 101 from within the implement 150 as indicated. More specifically, a mandrel or actuation rod within the implement 150 that is in physical communication with the actuator 175 and the platform 101 may be advanced or retracted by the actuator 175 to govern positioning of the platform. In this way, the extended profile platform 101 may be deployed for visualization once positioned within a patient's eye 350 and subsequently retracted to within the implement 150 for removal of the tool 100 (see FIG. 3).

Figure 2C:
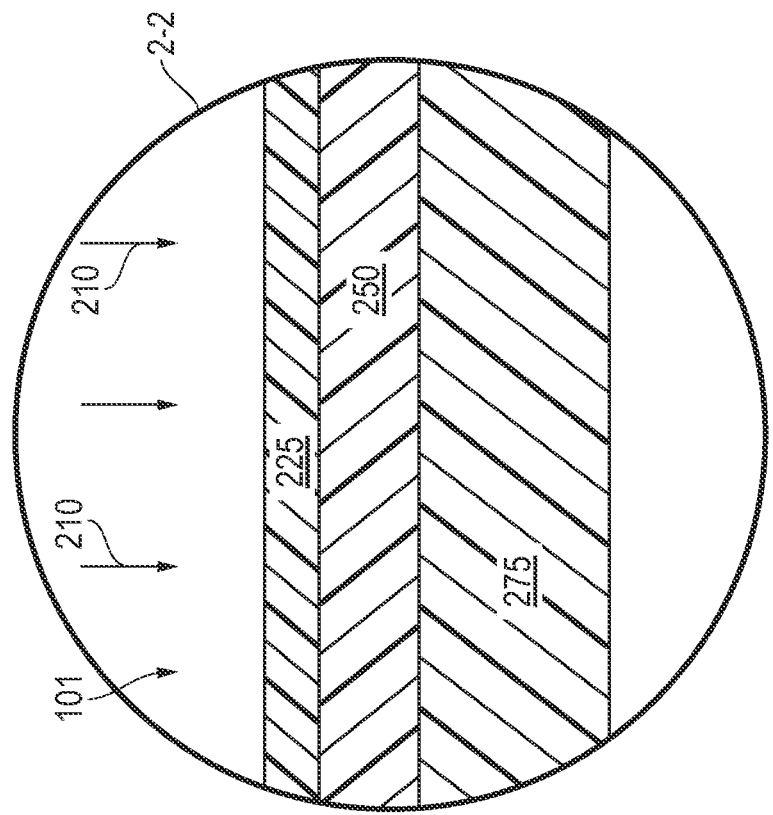
FIG. 2C is an enlarged side cross-sectional view taken from 2-2 of FIG. 2A and illustrating sensor layers of the imaging sheet.
Figure 2A:
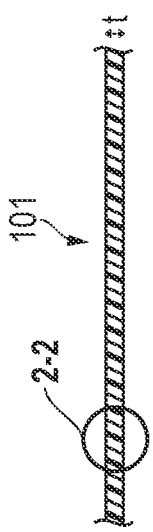
FIG. 2A is a side cross-sectional view of a thin-film imaging sheet of the platform of FIG. 1.

Referring now to FIG. 2A, a side cross-sectional view of the thin-film image capturing platform 101 of FIG. 1 is depicted. More specifically, the thin film image sensor sheet portion of the platform is illustrated which is of minimal thickness (t). That is, no underlying substrate is depicted. Regardless, the sheet is of less than about 0.05 mm in thickness (t) and likely remains so, even when adding the noted substrate. Thus, the ability to store a collapsible platform 101 within the implement 150 prior to use as illustrated in FIG. 4C is a practical undertaking.

Figure 2B:
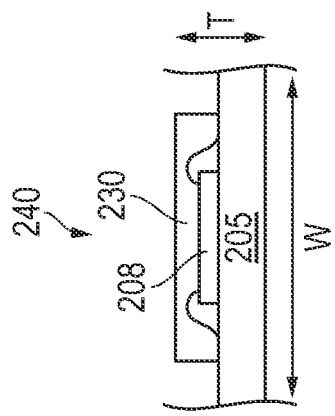
FIG. 2B is a side cross-sectional view of a microchip package within a housing of the tool of FIG. 1.

Referring now to FIG. 2B, with added reference to FIG. 1, a side cross-sectional view of a microchip package 240 is shown. The package 240 includes a chip 208 with sufficient memory for storing image capture data from the platform 101 of FIG. 2A. The package 240 also includes a conventional encapsulant 230, circuit board 205 and potentially other features contributing to an overall bulk footprint that would certainly be too large for accommodation within the implement 150. Unlike the collapsible platform 101, the package 240 is rigid and includes a thickness (T) and width (W) that are each likely over 1 mm. Nevertheless, there is sufficient space available within the housing 125 of the tool 100 to displace the package 240 away from the location of the thin-film platform 101 for storing in the housing 125. Conventional wiring or thin-film circuitry with metal traces running from the platform 101 and through the implement 150 to the housing 125 may be used to electronically couple the chip 208 to the platform 101.

Continuing with reference to FIG. 2B with added reference to FIG. 1, the package 240 may be a conventional CMOS (complimentary metal-oxide semiconductor) package that is well suited for image data management. An "off-the-shelf" package 240 may be suitable for use without the requirement of specially constructing a package 240 of tailored shape or sizing. Once more, the package 240 may include a wireless data transmitter to facilitate image data management and processing at a nearby mainframe location. Thus, the tool 100 may be a convenient wireless instrument for the surgeon with image generation being developed and presented on a nearby screen.

Referring now to FIG. 2C, an enlarged side cross-sectional view taken from 2-2 of FIG. 2A is shown illustrating sensor layers 225, 250, 275 of the thin-film platform 101. This illustrates an embodiment of image capture. Specifically, Faveon sensor architecture may be employed, utilizing a first layer 225 tailored to capture blue image data, a second layer 250 tailored to capture green image data, and a third layer 275 tailored to capture red image data. This stack attains the data as light 210 reaches and is accordingly absorbed at each layer. Depending on the overall surface area of the fully deployed platform 101 of FIG. 1, 10,000-100,000 pixels of data capture may be practically attained in this manner. Of course, there is no requirement of employing Faveon stacked architecture. For example, a non-stacked, Bayer sensor architecture may be preferred.

Referring now to FIG. 3, a side cross-sectional overview of a patient's eye 350 is illustrated during a vitrectomy procedure in which the imaging tool 100 of FIG. 1 is utilized. The surgery illustrated includes the positioning of instrumentation in an offset manner at the sclera 370. In this way, the more delicate cornea 390 and lens 380 may be avoided as well as delicate centrally located features at the back of the eye 350 such as the optic nerve 360 and retina 375. More specifically, a vitrectomy probe needle 325 is inserted through a preplaced cannula 330 and directed toward a region 310 where vitreous humor is to be removed. In the circumstance illustrated, the region 310 is somewhat offset and closer to the front of the eye 350 making it perhaps somewhat difficult for the surgeon or external imaging equipment to directly image. Thus, the positioning of the imaging tool 100 through another preplaced cannula 315 may be of particular benefit for this circumstance. A light instrument may also be positioned through another preplaced cannula at another offset location of the eye 350 to provide an aid to the visualization described below. Additionally, or alternatively, digitized light may be supplied directly through the electronics of the thin-film image capture platform 101 itself.

Continuing with reference to FIG. 3, with added reference to FIG. 1, the actuator 175 of the tool 100 may be manipulated by the surgeon to extend the platform 101 from within the implement 150. In the depicted illustration, the platform 101 can also be seen unfolding or unscrolled from a folded orientation to expose its surface toward the region 310 of interest. Thus, imaging of the region 310 may more directly take place. With the instrumentation in place, a suction may be applied through the vitrectomy needle 325 with the port 177 thereof being used for the uptake of the vitreous humor or other substances at the region 310. A direct visualization may be provided to the surgeon throughout this process by way of the tool 100 and platform 101.

Figure 4A:
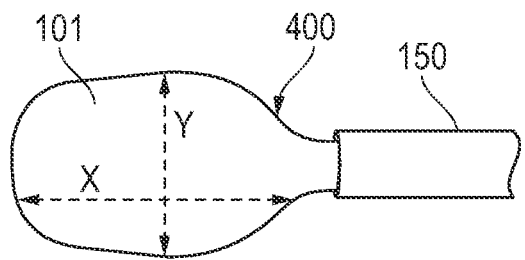
FIG. 4A is a top view of the thin-film image capturing platform of the tool of FIG. 3, fully extended to facilitate maximum imaging for the eye surgery.

Referring now to FIG. 4A, a top view of the thin-film image capturing platform 101 is shown in a fully extended and unfolded orientation to facilitate maximum imaging for the eye surgery of FIG. 3. By way of example only, the rectangular-like, unfolded face of the platform 101 may be greater than about 0.16 mm². That is, even where the inner diameter of the implement 150 is limited to about 0.4 mm as suggested above, this means that the platform 101 may be folded without any overlapping to match this inner diameter at 0.4 mm (e.g. the Y-axis). Of course, the platform 101 may fold over on itself and be even larger along the Y-axis. Further, the X-axis of the face of the platform 101 may be this large or even larger given that there is no practical concern about such folding along this axis. In one embodiment the X-axis of the platform 101 may span more than 5.0 mm. Regardless, for the illustrated example of an implement 150 with an inner diameter of about 0.4 mm, each axis (X, Y) of the platform 101 may be at least about 0.4 mm and thus, the surface area being at least about 0.16 mm². This is more than sufficient to support 10,000-to 100,000 pixel generation or greater with a state of the art thin-film sensor utilized as the platform 101.

Figure 4B:
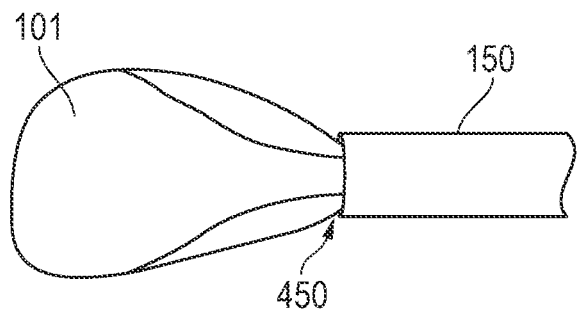
FIG. 4B is a top view of the thin-film image capturing platform during retraction into a needle implement of the tool.
Figure 4C:
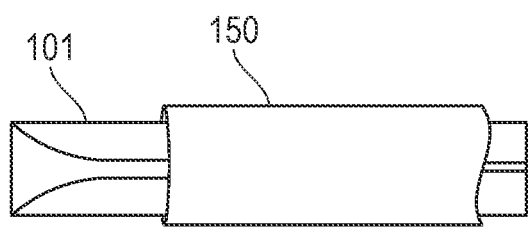
FIG. 4C is a top view of the thin-film image capturing platform fully collapsed for complete retraction into the needle implement for tool withdrawal from the eye.

Referring now to FIG. 4B, a top view of the thin-film image capturing platform 101 is illustrated during retraction into the needle implement 150. With added reference to FIG. 4A, note the deflection edges 400 of the platform 101. These edges 400 may be architecturally tailored to deflect and curl or fold inward upon meeting the interface 450 of the implement 150 during the withdrawal as directed by the actuator 175 through a mandrel/actuation rod as noted above (see FIG. 1). In one embodiment, in addition to the ramped deflection shape illustrated, the deflection edges 400 are of a more robust edge construction to promote deflection as illustrated and avoid damage to the platform 101 when forcibly withdrawing into contact with the interface 400.

Referring now to FIG. 4C, a top view of the thin-film image capturing platform 101 is shown fully collapsed. The platform 101 may now be completely retracted into the needle implement 150. In this manner, the entirety of the tool 100 of FIG. 1 may be removed from the eye 350 of FIG. 3 without concern over interference with the inner diameter of the preplaced cannula 315.

Figure 5:
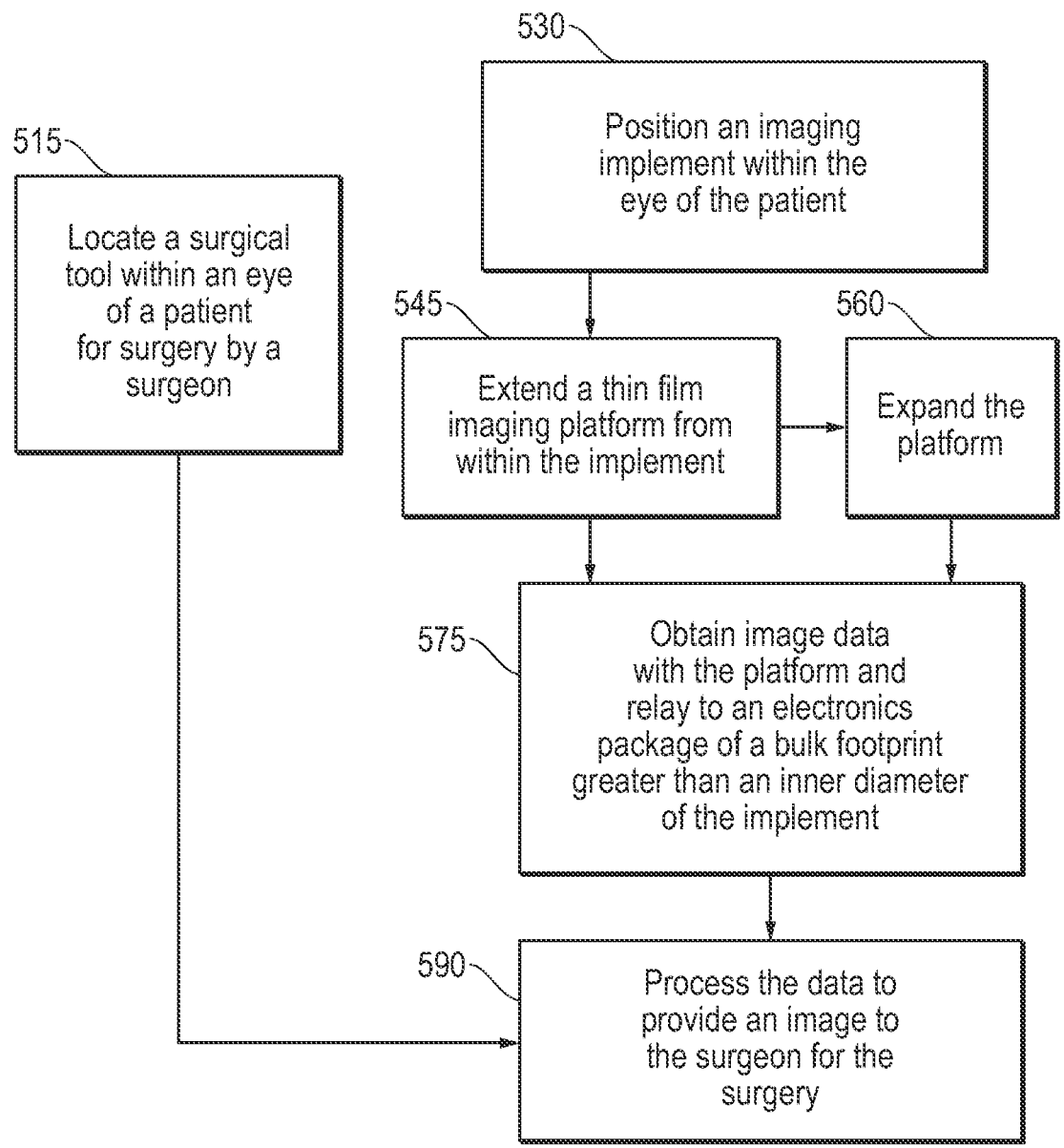
FIG. 5 is a flow-chart summarizing an embodiment of performing eye surgery with the aid of an imaging tool as illustrated in FIGS. 1 and 3.

Referring now to FIG. 5, a flow-chart is shown summarizing an embodiment of performing eye surgery with the aid of an imaging tool as illustrated in FIGS. 1 and 3. A surgical tool may be located within the eye as noted at 515. However, as an aid to the positioning and use of that tool, an imaging implement of another tool may also be positioned within the eye as noted at 530. Once positioned, a thin-film imaging platform may be deployed from within the implement and be exposed to the interior of the eye (see 545). This may also include expanding the platform from a folded or scrolled orientation as the platform is extended from the implement (see 560).

As indicated at 575, image data may be obtained by the platform and relayed to an electronics package at a displaced location (e.g. at the handpiece or housing of the associated tool). This package may be of a bulk footprint that is too large to have been accommodated within the implement. However, due to the displacement, no complicated redesign of the chipset is necessary. In one embodiment, the platform not only obtains image data but also serves as a light source to enhance the image data acquired. Further, in another embodiment, image data may be acquired from both sides or faces of the unfolded platform. Regardless, as indicated at 590, once the data is acquired and relayed it may be processed to provide a real-time image to the surgeon to promote safe and effective surgery.

Embodiments described hereinabove include tools and techniques that support direct imaging at an interior of a patient's eye during a surgical procedure and not mere reliance on indirect reverse mirrored imaging. This may be particularly beneficial when the surgical site includes offset, peripheral locations that are otherwise difficult to visually access. These tools and techniques allow for incisions and supporting pre-placed cannulas to remain of limited sizing to facilitate rapid healing following the surgery. Once more, image quality and/or management is not compromised. Rather, sizable, state-of-the-art chips and associated packaging may be fully utilized.

The preceding description has been presented with reference to several described embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

We claim:

1. An imaging tool to support eye surgery, the imaging tool comprising:
   a housing for physical manipulation by a surgeon during the eye surgery;
   a tubular implement of a given inner diameter and extending from the housing for reaching into an eye of a patient during the eye surgery, the housing accommodating a microchip with a bulk footprint greater than the given inner diameter; and
   a thin-film image capturing platform accommodated within the tubular implement, the thin-film image capturing platform extending from within the tubular implement for image capture of the eye during the eye surgery and configured for expanding upon the extending.

2. The imaging tool of claim 1, further comprising thin film image sensors of the thin-film image capturing platform electronically coupling to the microchip through the tubular implement.

3. The imaging tool of claim 2, wherein the coupling is attained through thin-film circuitry with conductive traces.

4. The imaging tool of claim 2, wherein the thin film image sensors acquire at least about 10,000 pixels of image data upon the extending and expanding.

5. The imaging tool of claim 2, wherein the thin film image sensors occupy more than about 5 mm of length within the given inner diameter of the tubular implement in advance of the extending therefrom.

6. An imaging tool to support eye surgery, the imaging tool comprising:
a housing for physical manipulation by a surgeon during the eye surgery;
a tubular implement of a given inner diameter and extending from the housing for reaching into an eye of a patient during the eye surgery;
a microchip accommodated by the housing and having a bulk footprint larger than the given inner diameter; and
a thin-film image capturing platform accommodated within the tubular implement, the thin-film image capturing platform extending from within the given inner diameter of the thin-film image capturing platform to acquire image data from within the eye and relay to the microchip during the eye surgery.

7. The imaging tool of claim 6, wherein the thin-film image capturing platform is less than about 0.05 mm in thickness and comprises thin-film image sensors on a support substrate.

8. The imaging tool of claim 6, wherein the given inner diameter is less than about 0.9 mm.

9. The imaging tool of claim 6, wherein the thin-film image capturing platform is tailored to unfold upon the extending to expose a face thereof to a region of the eye for the image data.

10. The imaging tool of claim 9, wherein the thin-film image capturing platform comprises ramped deflection edges to forcibly contact an interface of the tubular implement upon withdrawing of the thin-film image capturing platform into the given inner diameter, the deflection edges to promote re-folding of the thin-film image capturing platform during the withdrawing.

* * * * *